(12) United States Patent
Bigelow et al.

(10) Patent No.: US 6,462,561 B1
(45) Date of Patent: Oct. 8, 2002

(54) STANDOFF DISTANCE VARIATION COMPENSATOR AND EQUALIZER

(75) Inventors: Timothy A. Bigelow, Urbana, IL (US); Nasser Nidal Qaddoumi, Sharjah (AE); Reza Zoughi, Fort Collins, CO (US); Lawrence M. Brown, Manassas, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 26 days.

(21) Appl. No.: 09/616,971

(22) Filed: Jul. 14, 2000

(51) Int. Cl.[7] .............................................. G01R 27/32
(52) U.S. Cl. ........................ 324/637; 324/333; 324/369; 175/45
(58) Field of Search ........................... 324/96, 639, 644, 324/750, 753, 637, 22, 333, 338, 351, 346, 369; 175/45, 48, 152; 73/46, 152; 340/853; 342/357, 451; 701/213

(56) References Cited

U.S. PATENT DOCUMENTS

| | | |
|---|---|---|
| 4,286,216 A | 8/1981 | Auld et al. |
| 4,480,480 A | 11/1984 | Scott et al. |
| 4,629,319 A | 12/1986 | Clarke et al. |
| 4,920,385 A | 4/1990 | Clarke et al. |
| 5,103,106 A | 4/1992 | Goldberstein |
| 5,216,372 A | 6/1993 | Zoughi et al. |
| 5,278,498 A | 1/1994 | Vernon et al. |
| 5,384,543 A | 1/1995 | Bible et al. |
| 5,440,238 A | 8/1995 | Martens et al. |
| 5,539,322 A * | 7/1996 | Zoughi ........................ 324/644 |
| 5,574,379 A | 11/1996 | Darling |
| 5,748,003 A | 5/1998 | Zoughi et al. |
| 5,859,535 A | 1/1999 | Liu |
| 5,892,357 A * | 4/1999 | Woods ........................ 324/96 |
| 5,904,210 A * | 5/1999 | Stump ........................ 175/45 |
| 5,939,889 A | 8/1999 | Zoughi et al. |
| 6,005,397 A | 12/1999 | Zoughi et al. |

* cited by examiner

Primary Examiner—Michael Sherry
Assistant Examiner—Trung Q. Nguyen
(74) Attorney, Agent, or Firm—Howard Kaiser

(57) ABSTRACT

An inventively enhanced near-field sensor includes circuitry which removes variation in standoff distance (of the sensor from the inspected object) as a factor in the inspection system readings. An original output voltage which varies linearly according to standoff distance is, modified and added to a counterbalancing output voltage which equivalently but oppositely varies linearly according to standoff distance, resulting in a constant output voltage regardless of standoff distance. For calibration purposes, a third output voltage can also be summed along with the modified output voltage and the counterbalancing output voltage. Since the effect of surface variation is nullified, the practitioner can more truly assess the interior physical condition of the inspected object, knowing that the object's surface roughess is rendered irrelevant.

37 Claims, 6 Drawing Sheets

STANDOFF DISTANCE VARIATION COMPENSATOR AND EQUALIZER

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

The present invention relates to the nondestructive testing or evaluation of physical properties of materials, more particularly to methods and apparatuses for accomplishing near-field inspection of materials, such as involving utilization of microwave radiation in association with materials such as metallic or composite materials.

Various kinds of near-field microwave inspection have been conducted with respect to various kinds of structures (e.g., composite or metallic structures) having an extended surface area. Generally, a near-field probe (for example, a open-ended rectangular waveguide probe or an open-ended coaxial probe) is used in conventional practice of near-field microwave inspection. Typically, the microwave inspection inherently incorporates or assumes a "standoff distance" or "liftoff" of the near-field probe in relation to the surface area of the material being inspected.

The measurement results are usually sensitive to the changes in this standoff distance. Sometimes a change in the standoff distance is related to variation in surface roughness (or, synonymously expressed, surface height). For instance, in the case of glass reinforced epoxy composites, the change in the standoff distance can be caused by surface roughness/height variations in the composite skin.

It is generally important to distinguish between or among various types of defects. For instance, in the case of a composite laminate, it may be desirable that an internal defect such as a layer-layer disbond be distinguished from a defect on the surface such as related to impact damage. In order to differentiate between or among internal and external defects, the influence of standoff distance variation must somehow be accounted for.

SUMMARY OF THE INVENTION

In view of the foregoing, it is an object of the present invention to provide method and apparatus for effectuating near-field microwave nondestructive testing of an object in such a way as to more capably distinguish between internal physical characteristics and external physical characteristics.

The present invention features the neutralization of the effect of surface variation of the object in the context of near-field sensing. Provided by the present invention is a circuit which accounts for standoff distance variation and eliminates its influence from the final inspection system output. The inventive compensatory and equalizing circuit has been designed and successfully tested by the U.S. Navy and Colorado State University in association with open-ended rectangular waveguide probes.

According to typical embodiments of the present invention, the inventive apparatus is used in association with a sensing device which is capable of producing a nonconstant device signal for inspecting an object. The sensing device's nonconstant device signal varies in accordance with the distance of the sensing device from the object. The inventive apparatus comprises means for rendering the sensing device capable of producing a constant device signal at least until reaching said object, wherein the constant device signal is constant regardless of the distance.

According to many inventive embodiments, the inventive means for rendering includes: means for producing a nonconstant counteractive output signal, the nonconstant counteractive signal varying in accordance with the distance; means for modifying the nonconstant device signal so as to become a nonconstant modified device signal which is commensurate with the nonconstant counteractive signal; and, means for combining signals, the means for combining signals including means for combining the nonconstant counteractive signal and the nonconstant modified device signal. The constant device signal is based on the combining of the nonconstant counteractive signal and the nonconstant modified device signal.

According to frequently preferred inventive practice, the inventive means for rendering also includes means for producing a constant offset signal. Thus, the means for combining signals includes means for combining the nonconstant counteractive signal, the nonconstant modified device signal and the constant offset signal. The constant device signal is based on the combining of the nonconstant modified device signal, the nonconstant counteractive signal and the constant offset signal.

In typical inventive practice, the nonconstant device signal, the nonconstant modified device signal and the nonconstant counteractive each vary linearly according to distance. Frequent inventive practice prescribes such linear variation in terms of voltage value. The "constancy" characteristic of both the constant device signal and the the constant offset signal presupposes a nonvarying linearity of each constant signal, freqently manifested in inventive practice as a constancy (i.e., single-valued linearity or invariability) in voltage value. In contrast, the "nonconstancy" characteristic of the nonconstant device signal, the nonconstant modified device signal and the nonconstant counteractive signal entails a varying linearity of each nonconstant signal, frequently manifested in inventive practice as a nonconstancy (i.e., plural-valued linearity or linear variability) in voltage value.

Usually, the nonconstant device signal varies linearly in accordance with the standoff distance; however, the inventive principles are still applicable whether the nonconstant device signal varies linearly or nonlinearly in accordance with the standoff distance. In fact, the present invention can be practiced regardless of whether the nonconstant device signal, the nonconstant modified device signal and the nonconstant counteractive signal vary linearly or nonlinearly according to distance. If, for instance, the initial voltage output varies as a nonlinear function of standoff distance, according to this invention a counterbalancing voltage output can be effected which equally but oppositely varies as a nonlinear function of standoff distance. Similarly, if the initial voltage output varies as a linear function of standoff distance, according to this invention a counterbalancing voltage output can be effected which equally but oppositely varies as a linear function of standoff distance.

Featured by the present invention is the provision of a voltage commensurate with the inspected material's surface roughness, and the addition of such provided voltage to, or the subtraction of such provided voltage from, the voltage detected by the microwave detector. In other words, according to this invention, a voltage is provided which is proportional to the surface roughness and is then added to or subtracted from the voltage detected by the microwave detector; such proportionality of voltage with respect to surface roughness can equivalently be considered to be a proportionality of voltage with respect to standoff distance. In this way, the present invention renders the final output voltage independent of surface roughness variations, which are typically slight but which can manifest diverse degrees and kinds of irregularity.

A near-field microwave device typically produces a voltage output signal which is a linear function of standoff distance. According to the present invention, potentiometer circuitry is provided to produce a voltage output signal which is a linear function of standoff distance, but which is oppositely sloped in comparison with the voltage output signal of the microwave device. Thus, if the microwave device's voltage output linearly increases in accordance with standoff distance, the inventive potentiometer circuitry's voltage output linearly decreases in accordance with standoff distance; on the other hand, if the microwave device's voltage output linearly decreases in accordance with standoff distance, the inventive potentiometer circuitry's voltage output linearly increases in accordance with standoff distance.

Further, according to the present invention, the slope of the microwave device's voltage output is rendered not only opposite to but also equal in magnitude to that of the potentiometer circuitry's voltage output. In this regard, the microwave device's voltage output is multiplied by an appropriate multiplication factor, thereby yielding a slope which is not only oppositely signed but which also has a magnitude which is equal to that of the potentiometer circuitry's output voltage.

Therefore, in accordance with this invention, when the microwave device's voltage output is multiplicatively modified and then counteractively (e.g., additively or subtractively) associated with the potentiometer circuitry's voltage output, the result is a constant voltage output irrespective of standoff distance. If graphically visualized as voltage output (y-axis) as a function of standoff distance (x-axis), the voltage output of the near-field microwave device, as inventively modified, is zero-sloped (i.e., horizontal).

The present invention thus enhances or improves the inspection capability of near-field microwave nondestructive testing techniques (such as those which implement open-ended rectangular waveguide sensors or open-ended coaxial sensors) for detection of interior flaws (e.g., manufactured or in-service produced flaws) in materials (such as multi-layered dielectric composites) in which a certain degree of surface roughness is present.

Although the present invention is applicable to diverse types of materials such as generally categorized as composite materials, it is especially beneficial when practiced with respect to composite laminates, wherein it is desirable to distinguish internal anomalies (such as associated with bonding of lamina) from external (surface) irregularities. Currently, there is no known efficient technique for continuously correcting for standoff distance variations caused by surface roughness in structures (such as dielectric composite structures) as a near-field probe (such as an open-ended rectangular waveguide aperture probe) scans over a material (such as a composite material). The new circuitry according to this invention monitors standoff distance variations (e.g., due to surface roughness) and electronically corrects the microwave detector output voltage for this variation.

Other objects, advantages and features of this invention will become apparent from the following detailed description of the invention when considered in conjunction with the accompanying drawings.

BRIEF DESCRIPTION OF THE DRAWINGS

In order that the present invention may be clearly understood, it will now be described, by way of example, with reference to the accompanying drawings, wherein like numbers indicate the same or similar components, and wherein:

FIG. 5 is illustrative of how standoff dependency may be removed in accordance with the present invention.

DETAILED DESCRIPTION OF THE INVENTION

Figure 1:
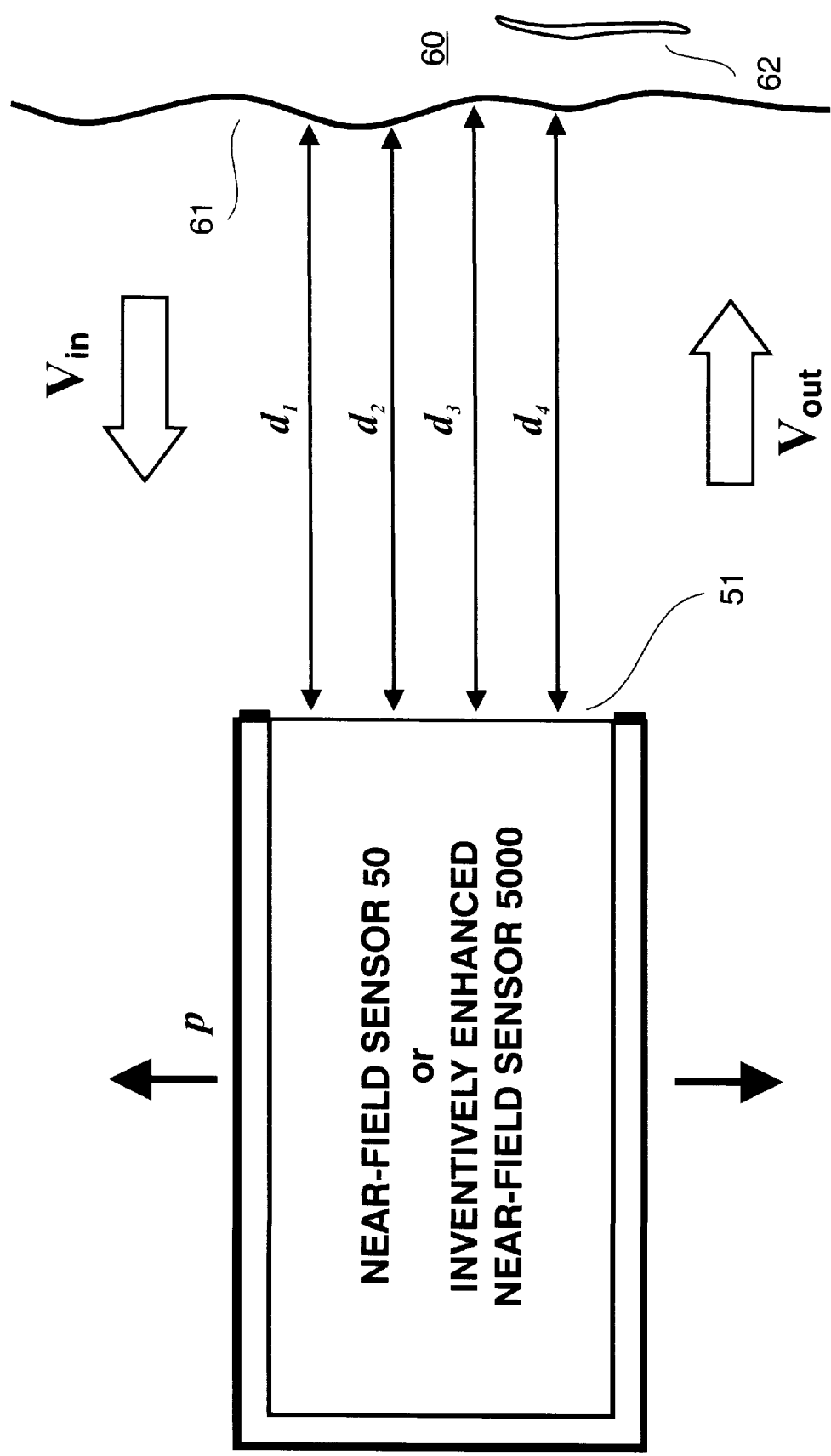
FIG. 1 is a diagrammatic representation of implementation of a near-field microwave sensor with respect to an object having a surface characterized by a degree of irregularity.

Referring now to FIG. 1, conventional near-field sensor 50 is a microwave detector such as the kind which includes an oscillator and a crystal diode detector. Near-field sensor includes an open-ended probe (such as a rectangular waveguide probe or a coaxial probe) having a probe open end 51 for scanning material 60 having material surface 61. Near-field scanning of inspected material 60 by sensor 50 is typically performed while sensor 50 is caused to move in a bidirection p which is generally parallel to material surface 61, probe open end 51 thereby generally maintaining a standoff distance d from material surface 61.

The electromagnetic radiation (microwave radiation, in this example) is caused by near-field sensor 50 to be transmitted to material surface 61 and at least partially through the thickness of material 60, and then return to near-field sensor 50. Output voltage $V_{out}$ is the signal which reachs material surface 61. Upon penetration of material 60, output voltage $V_{out}$ is altered by the internal physical characteristics of material 60. Thus, input voltage $V_{in}$, the signal which returns to near-field sensor 50, is altered as compared with output voltage $V_{out}$. The problem with conventional near-field sensor 50 is that output voltage $V_{out}$ is variable due to variability of material surface 61, thus rendering readings based on input voltage $V_{in}$ less meaningful, less accurate or more problematical.

Material surface 61 is not perfectly smooth or flat, and is in fact characterized by surface irregularities ("surface roughness") which are significant enough to appreciably change output voltage $V_{out}$ (the voltage emanating from near-field sensor 50), since such voltage varies in accordance with distance d. The output voltage $V_{out}$ of near-field sensor 50 is variable in a manner commensurate with the variability of standoff distance d at different points along material surface 61, e.g., unequal standoff distances $d_1$, $d_2$, $d_3$ and $d_4$ as shown in FIG. 1.

For illustrative purposes, material 60 is shown in FIG. 1 to have an internal defect 62, such as a localized disengagement (disbonding) between two layers of material 60 if material 60 is a composite laminate. Because of the variability of standoff distance d and hence of the output voltage $V_{out}$, of near-field sensor (e.g., microwave detector) 50, when utilizing conventional near-field sensor 50 it will be difficult or impossible to distinguish between internal aberrations of material 60, such as defect 62, from external aberrations and irregularities in general of material 60 which are manifested at material surface 61. This is because, when input voltage $V_{in}$ is reflected from material 60 and returned to near-field sensor 50 for detection, it will be difficult or impossible to determine to what extent the change in $V_{in}$ vis-a-vis $V_{out}$ is attributable to the internal physical characteristics of material 60, and to what extent such change is attributable to the roughness of material surface 61.

However, let us consider the near-field sensor shown in FIG. 1 to be inventively enhanced near-field sensor 5000, rather than conventional near-field sensor 50. Inventively enhanced near-field sensor 5000 produces the same output voltage $V_{out}$ regardless of which location on material surface 61 output voltage $V_{out}$ has reached—equivalently expressed, regardless of distance d. In other words, at least until output voltage $V_{out}$ has reached material surface 61, output voltage $V_{out}$ will be constant. At the point at which output voltage $V_{out}$ begins to penetrate inspected material 60, output voltage $V_{out}$ is subject to change. Hence, according to the present invention, the value difference of input voltage $V_{in}$ in comparison with output voltage $V_{out}$ is assured to be entirely attributable to internal physical characteristics of inspected material 60, and not the least bit attributable to surface variation of material surface 61. In contrast to readings based on input voltages $V_{in}$ for near-field sensor 50, readings based on input voltages $V_{in}$ for inventively enhanced near-field sensor 5000 are free of distortions associated with nonconstancy of output voltage $V_{out}$.

Figure 2:
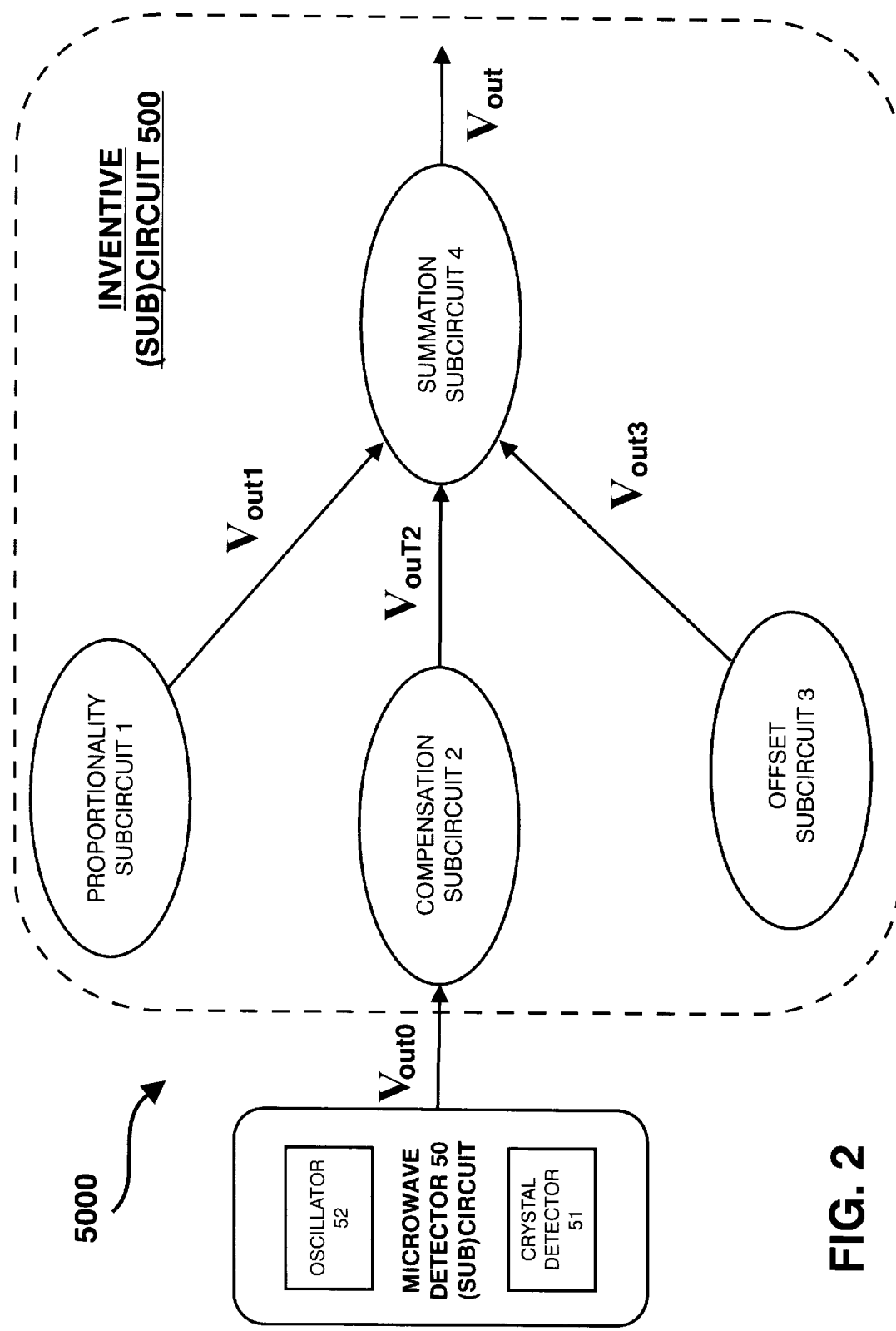
FIG. 2 is a block diagram of an embodiment of a standoff distance variation compensator/equalizer in accordance with the present invention.

Still referring to FIG. 1 and also referring to FIG. 2, near-field sensor includes a crystal diode detector 51 and an oscillator 52. The objective of inventive circuitry 500 is to inventively enhance the near-field sensor (e.g., waveguide probe or other microwave detector or device) 50 circuitry so as to effectuate compensation of the voltage output $V_{out0}$ as measured from microwave device 50 with respect to changes in the standoff distance d from the (waveguide) opening 51 to the surface 61 of material 60.

In the absence of the electronic apparatus 500 in accordance of the present invention, near-field sensor 50 produces an output voltage $V_{out0}$ (such as would be received at terminal or point 22 shown in FIG. 4) which is proportional to standoff distance d. When inventively enhanced through connection with inventive circuitry 500, conventional near-field sensor 50 becomes inventively enhanced near-field sensor 5000 which produces an inventively corrected output voltage $V_{out}$ which is the same regardless of standoff distance d. Inventively enhanced microwave detector 5000 has an overall circuitry which comprises the combination of the original microwave detector 50 circuitry and the inventive circuitry 500.

In this regard, the present invention takes advantage of the fact that the output voltage $V_{out0}$ of microwave device 50 changes as a linear function of standoff distance d. Thus, according to this invention, the output voltage $V_{out0}$ of microwave device 50 can be corrected by incorporating in or connecting to the circuitry of microwave device 50 a spring-loaded, piston potentiometer 100, such as shown in FIG. 3 and FIG. 4, which produces a linear output voltage based on the distance from microwave device 50 to the surface 61 of the inspection material 60.

Figure 3:
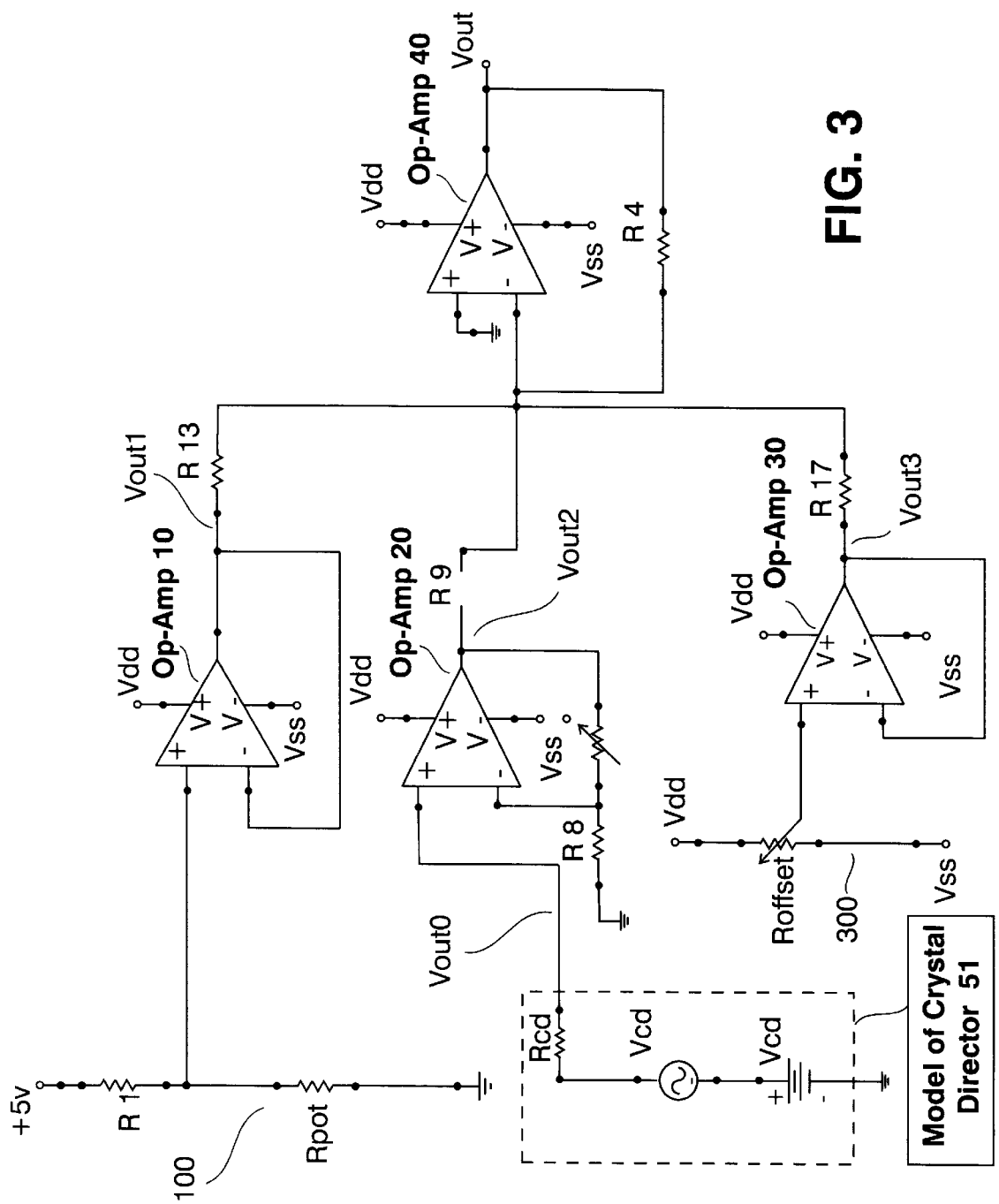
FIG. 3 is a circuit diagram of the inventive embodiment shown in FIG. 2.
Figure 4:
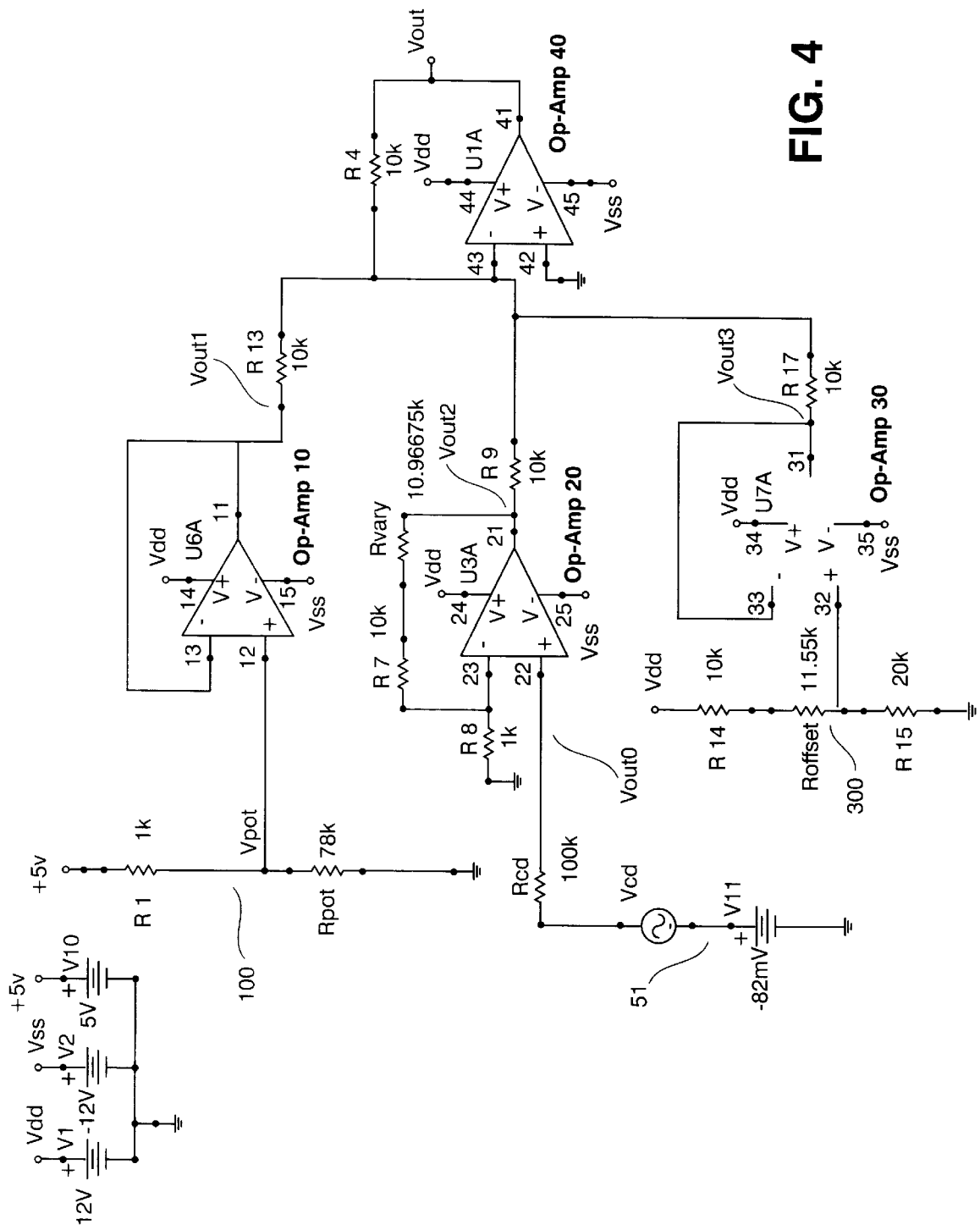
FIG. 4 is a more detailed version of the circuit diagram shown in FIG. 3.

Still with reference to FIG. 1 and FIG. 2 and particularly with reference to FIG. 3 and FIG. 4, microwave device 50 includes crystal (diode) detector 51. Crystal detector 51 is akin to a voltmeter, and is an integral part of microwave device 50. The model of crystal detector 51 shown in FIG. 3 and FIG. 4 is for electromagnetic radiation having a particular frequency; however, the ordinarily skilled artisan understands in the light of this disclosure that such a model depends on the frequency (or frequencies) of the system, and that, more generally, the physical characteristics of the inventive circuitry 500 are a function of frequency. Various aspects of inventive circuit 500 are modeled based on the involved frequency or frequencies, and the models should be changed accordingly.

Inventive circuit 500 includes proportionality subcircuit 1, compensation subcircuit 2, offset subcircuit 3 and summation subcircuit 4. Proportionality subcircuit 1 includes potentiometer 100, operational amplifier (op-amp) 10 and resistor R13. Compensation subcircuit 2 includes operational amplifier (op-amp) 20 and resistor R9. Offset subcircuit 3 includes operational amplifier (op-amp 30) and resistor R17. Operational amplifier 30 includes includes offset element 300, which includes resistor R14, variable resistor $R_{offset}$ and resistor R15. Summation subcircuit 4 includes operational amplifier (op-amp) 40.

Potentiometer 100 includes resistor R1 and resistor Rpot. Operational amplifier 10 includes point (electrical contact) 11, point 12, point 13, point 14 and point 15. Operational amplifier 20 includes resistor R7, resistor R8, variable resistor $R_{vary}$, point 21, point 22, point 23, point 24 and point 25. Operational amplifier 30 includes resistor R14, variable resistor $R_{offset}$, resistor R15, point 31, point 32, point 33, point 34 and point 35. Operational amplifier 40 includes resistor R4, point 41, point 42, point 43, point 44 and point 45.

Operational amplifier 10 acts as a buffer circuit isolating the potentiometer 100 portion from the rest of inventive circuit 500. Resistor $R_{pot}$ models the variable resistance of potentiometer 100 as the standoff distance d changes.

Operational amplifier 20 performs two functions. First, it amplifies the signal from crystal detector 51. Secondly, as further explained herein with reference to FIG. 5, by adjusting the variable resistor $R_{vary}$, the overall circuitry can be "balanced" to remove the effect of standoff variation. This represents a first type of "calibration" which is effectuated according to the present invention. According to typical inventive practice, variable resistor $R_{vary}$ is inventively set in accordance with a particular inspected material 60.

Operational amplifier 30 acts as a buffer circuit for the offset voltage resistor network, viz., offset subcircuit 3. Resistor $R_{offset}$ can be used to set the overall output voltage $V_{out}$ to zero or any other selected value. In other words, resistor $R_{offset}$ is selected so as to yield an output voltage $V_{out}$ having a desired value which represents a reference voltage for inventively enhanced near-field sensor 5000. This represents a second type of "calibration" which is effectuated according to the present invention. Variable resistor $R_{offset}$ can be inventively set to yield a desired value of output voltage $V_{out}$.

Reference voltage $V_{out}$ is the constant voltage existing until the electromagnetic (e.g., microwave) radiation emanating from inventively enhanced near-field sensor 5000 reaches surface 61 of inspected material 60, at which point the voltage, as it proceeds internally in material 60, may be affected (altered) in accordance with the physical characteristics of material 60. The electromagnetic radiation in its altered form (e.g., altered voltage) returns to near-field sensor in feedback loop fashion. This change in the properties of the signal (e.g., change in voltage) is detected by crystal detector 51 and is measured by inventively enhanced near-field sensor 5000 with reference to the reference voltage $V_{out}$. Operational amplifier 30, by producing output voltage $V_{out3}$, thus serves the purpose of setting voltage $V_{out}$ at a desired value for use as a reference voltage, with which the voltage returned to and detected by inventively enhanced near-field sensor 5000 is compared. Setting voltage $V_{out}$ as a zero-valued reference voltage may be preferable for many inventive embodiments.

Summation subcircuit 4 includes operational amplifier 40 which adds the voltages $V_{out1}$, $V_{out2}$ and $V_{out3}$ together to give the final output voltage $V_{out}$. Voltage $V_{out1}$ is the output voltage from proportionality subcircuit 1 (which includes operational amplifier 10 and potentiometer 100). Voltage $V_{out2}$ is the output voltage from compensation subcircuit 2 (which includes operational amplifier 20).

As further explained hereinbelow, voltage $V_{out2}$ is equal to the product of an inventively determined factor $[1+(R_{vary}+R7)/R8]$ and the output voltage $V_{out0}$ from crystal detector 51. Voltage $V_{out3}$ is the output voltage from the offset voltage resistor network, viz., offset subcircuit 3 (which includes operational amplifier 30). In inventive practice, resistor R4 can be replaced with a non-linear component, if variable gain is required.

The inventive circuit 500 for correcting the output voltage $V_{out0}$ of the microwave device's crystal detector 51 is shown in summary form in FIG. 3 and in greater detail in FIG. 4. Basically, inventive standoff compensating/equalizing circuit 500 involves four input/output subcircuits, as follows: (i) the voltage $V_{pot}$, which is output from potentiometer 100 and which reflects changes in standoff distance d, is input into operational amplifier 10, with a resultant voltage $V_{out1}$ output from operational amplifier 10; (ii) the voltage $V_{out0}$, which is output from microwave device 50, is input into operational amplifier 20, with a resultant voltage $V_{out2}$ output from operational amplifier 20; (iii) the voltage $V_{off}$, which is output from offset element 300 (between resistor $R_{off}$ and resistor R15) and which is used to produce a zero reference (or other selected value reference) output voltage $V_{out}$, is input into operational amplifier 30, with a resultant voltage $V_{out3}$ output from operational amplifier 30; (iv) the voltages $V_{out1}$, $V_{out2}$ and $V_{out3}$, which are input from operational amplifiers 10, 20 and 30, respectively, are input into operational amplifier 40, with a resultant voltage $V_{out}$ output from operational amplifier 40, which is the voltage output by inventively enhanced near-field sensor 5000 during operation thereof with respect to material 60 while fronting material surface 61.

In other words, inventive circuit 500 includes three operational amplifiers (i.e., operational amplifiers 10, 20 and 30) which are used to condition the corresponding input signals (i.e., voltages $V_{pot}$, voltage $V_{out0}$, and voltage $V_{off}$, respectively). Additionally, inventive circuit 500 includes a final stage operational amplifier, viz., operational amplifier 40, to add the three output signals (i.e., voltages $V_{out1}$, $V_{out2}$ and $V_{out3}$) together and thereby produce a final output voltage $V_{out}$.

More specifically, operational amplifier 10 is a unity gain or voltage follower of the input voltage $V_{pot}$ from potentiometer 100. Operational amplifier 10 acts as a buffer to isolate potentiometer 100 from the rest of inventive circuit 500. Potentiometer 100 touches or contacts material surface 61 and thereby tracks the surface roughness of material surface 61. The spring-loaded potentiometer 100 is modeled at a 78 kΩ variable resistor, $R_{pot}$, in series with a 1 kΩ resistor R1 connected to a +5 Volt DC power supply. The 1 kΩ resistor R1 acts in conjunction with the $R_{pot}$ as a voltage divider. The voltage $V_{pot}$ to the noninverting input terminal of operation amplifier 10, indicated at point (location or terminal) 12, is taken from the point at the potentiometer, $V_{pot}$, as shown in FIG. 4. The output of operational amplifier 10, point 11, follows the input voltage.

Operational amplifier 20 handles the input $V_{out0}$, output from microwave crystal detector 51 of microwave device 50. The model for the microwave crystal detector 51 is a 100 kΩ resistor $R_{cd}$ in series with a variable voltage input $V_{cd}$ and a −82 mVolt DC power supply. Crystal detector 51 is connected to v the noninverting input of operational amplifier 20 at input 22 as shown in FIG. 4. The negative feedback loop of operation amplifier 20 contains a 10.96 kΩ resister $R_{vary}$ in series with a 10 kΩ resistor R7 connected to the inverting terminal at point 23. The inverting terminal of operational amplifier 20 is connected to ground through a 1 kΩ resistor R8.

Operational amplifier 20 acts a linear multiplier for the voltage $V_{out0}$, seen from the crystal detector 51 circuit. The output voltage $V_{out2}$ for operational amplifier 20 at point 21 is equal to $[1+(R_{vary}+R7)/R8]$ times the output voltage input $V_{out0}$ of crystal detector 51. By selecting the appropriate value for $R_{vary}$, the voltage $V_{out0}$ from crystal detector 51 can be multiplied by the appropriate factor $[1+(R_{vary}+R7)/R8]$ so as to obtain a voltage $V_{out2}$ which compensates (offsets or counterbalances) the output voltage $V_{out1}$, which is derived from the voltage $V_{pot}$ input from potentiometer 100, which in effect measures the standoff distance d. That is:

$$V_{out2}=V_{out0}\times[1+(R_{vary}+R7)/R8].$$

The output voltage $V_{out2}$ from the operational amplifier 20 is equal but opposite in slope with respect to the output voltage $V_{out1}$ from operational amplifier 10. That is, the absolute value of the slope described by $V_{out1}$ equals the absolute value of the slope described by $V_{out2}$. In the absence of an offset output voltage $V_{out3}$, the sum of $V_{out1}$ and $V_{out2}$ will be a constant k. That is, $V_{out1}+V_{out2}=k$. The equal and opposite slopes of $V_{out1}$ and $V_{out2}$ cancel each other, leaving a net voltage k.

Operational amplifier 30, like operational amplifier 10, is also a unity gain follower. Operational amplifier 30 is a unity gain follower for the offset voltage $V_{offset}$ taken at the point between $R_{offset}$ and R15 as input to the noninverting input terminal at point 32. The 11.55 kΩ variable resistor $R_{offset}$ is in series with a 10 kΩ resister R14 and a 20 kΩ resister R15 connected to a +5 Volt DC power supply. The variable resistor $R_{offset}$ allows for adjusting of the final output voltage of the operational amplifier 40, viz., output voltage $V_{out}$, to 0 Volts when the inventively enhanced microwave circuit 5000 is calibrated. During calibration, inventively enhanced microwave circuit 5000 can be at any acceptable fixed calibration standoff distance $d_0$ from the inspection material surface 61 in the near field; inventively enhanced microwave circuit 5000 can be in contact with material surface 61 (i.e., wherein the standoff distance $d_0$ equals zero) or at a fixed distance $d_0$ greater than zero.

In other words, according to typical inventive practice, offset subcircuit 3, which includes operational amplifier 30, outputs a voltage $V_{out3}$ which serves as a calibrational "zeroing" offset with respect to the sum of output voltages $V_{out1}$, $V_{out2}$ and $V_{out3}$ because the sum of output voltages $V_{out}$ and $V_{out2}$ is k. That is, since $V_{out1}+V_{out2}=k$, the value of $V_{out3}$ will determine the value of $V_{out}$ in the equation $V_{out}=V_{out1}+V_{out2}+V_{out3}$. Otherwise expressed, $V_{out}=k+V_{out3}$. If $V_{out3}$ equals −k, then $V_{out}$ equals zero. It is thus seen that, according to this invention, $V_{out3}$ can be selectively set during calibration to obtain a value of "zero" or practically any other desired value of the overall output voltage $V_{out}$. Since $|V_{out}|=V_{out1}+V_{out2}+V_{out3}$, and $V_{out1}+V_{out2}=k$, if $V_{out3}=-k$, then $V_{out}=0$.

According to many inventive embodiments, operational amplifier 40 is simply a voltage adder. The 10 kΩ resistor R4 in the negative feedback loop has a 10 kΩ resistance, equal to the 10 kΩ resistance for each of resistors R13, R9 and R17, which look at the corresponding outputs ($V_{out1}$, $V_{out2}$ and $V_{out3}$, respectively) from the three previous amplifiers (operational amplifiers 10, 20 and 30, respectively). Hence, the last stage of inventive circuit 500, viz., summation subcircuit 4 (which includes operational amplifier 40), simply adds together the three output voltages $V_{out1}$, $V_{out2}$ and $V_{out3}$, as follows:

$$V_{out}=-(V_{out1}+V_{out2}+V_{out3})$$

The above equation states that, according to the inventive embodiment described herein and to some other inventive embodiments, $V_{out}$ equals negative the quantity $V_{out1}$ plus $V_{out2}$ plus $V_{out3}$. It is noted that, according to some embodiments of the present invention, $V_{out}$ equals positive the quantity $V_{out1}$ plus $V_{out2}$ plus $V_{out3}$; that $V_{out}=V_{out1}+V_{out2}+V_{out3}$.

Output voltage $V_{out}$ represents the overall output voltage which reaches material surface 61. When the microwave radiation having voltage $V_{out}$ penetrates material 60, it will be affected by irregular internal physical manifestations therein such as internal defect 62 shown in FIG. 1. Defect 62 will cause a change in voltage, ΔV. Thus, input voltage $V_{in}$ (which returns to near-field sensor 50) will deviate from output voltage $V_{out}$ (which emits from near-field sensor 50) by voltage change ΔV (which is attributable to an internal physical characteristic such as internal defect 62). That is, $V_{in}=V_{out}+ΔV$. In the absence of an internal aberration or irregular physicality (e.g., internal defect 61) which affects the voltage by a factor of ΔV, ΔV=0, and hence $V_{in}=V_{out}$. If material 60 is physically homogeneous, then ΔV=0; hence, $V_{in}=V_{out}+ΔV=V_{out}+0=V_{out}$. If material 60 is physically nonhomogeneous in some respect, then, in relation to such nonhomogeneity, ΔV>0 or ΔV<0; hence, since $V_{in}=V_{out}+ΔV$, it follows that $V_{in}>V_{out}$ or $V_{in}<V_{out}$.

To summarize, by correctly selecting the multiplier value, $R_{vary}$, the output voltage $V_{out1}$ derived from the potentiometer 100 measuring standoff can be completely compensated. Thus, as the standoff distance d from the material surface 61 to the waveguide opening 51 changes, the output voltage. $V_{out}$ of the inventive circuit 500 (and hence, of the inventively enhanced near-field sensor 5000) will remain constant. By selecting $R_{offset}$ appropriately, the constant output voltage $V_{out}$ can be set to 0 Volts (or to another desired voltage value). Once the two variable resistors $R_{vary}$ and $R_{offset}$ are set in an inventive calibration procedure, then the near-field sensor 5000 device can be used for inspection of defects in material 60. At this point, any changes in the output voltage $V_{out}$ are resultant of changes in material properties of material 60, not of standoff distance d.

Figure 5:
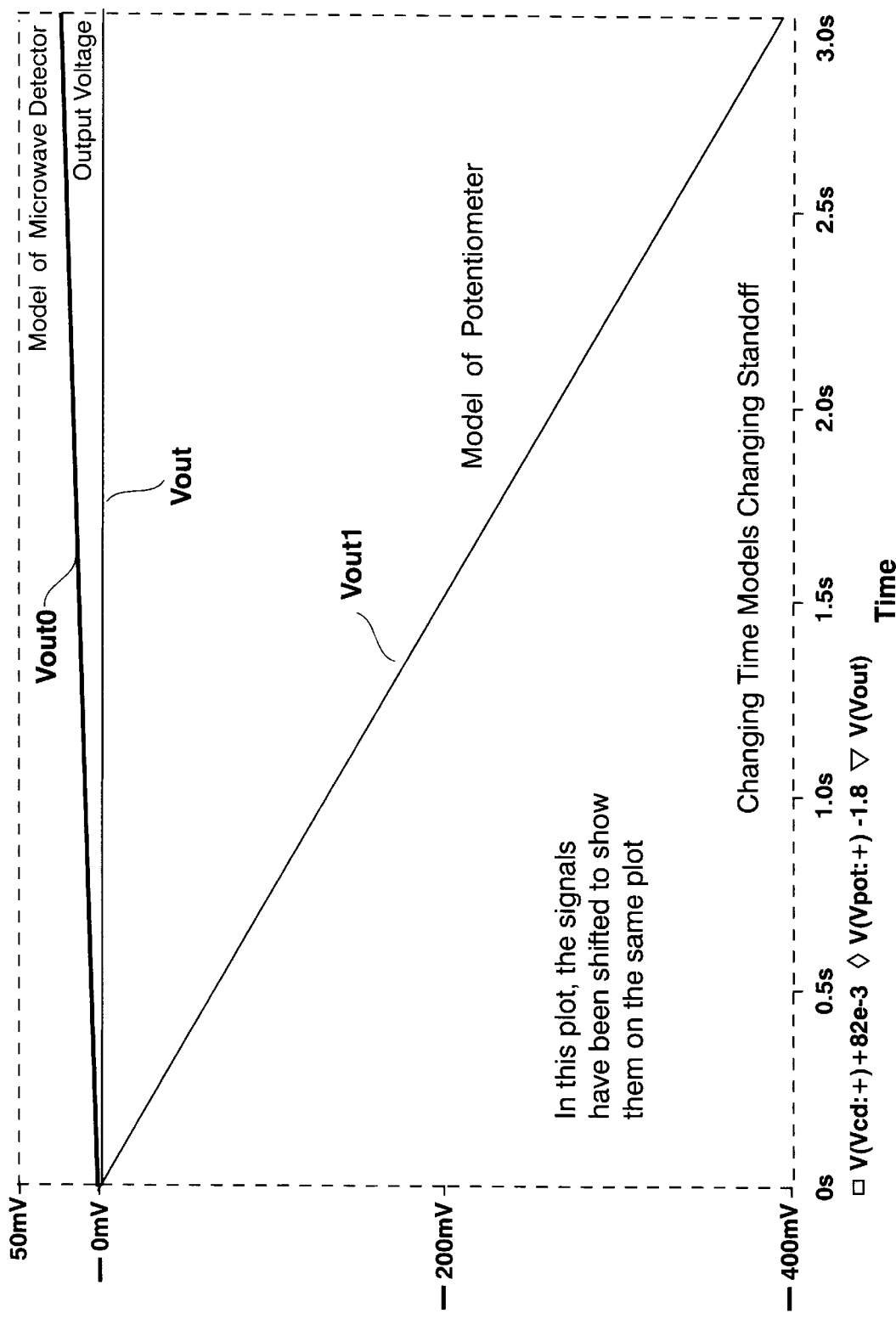
FIG. 5 is a graph, obtained using a computer simulation program for electronic circuitry, of voltage (y-axis) versus time (x-axis), wherein time is representative of standoff distance.
Figure 6:
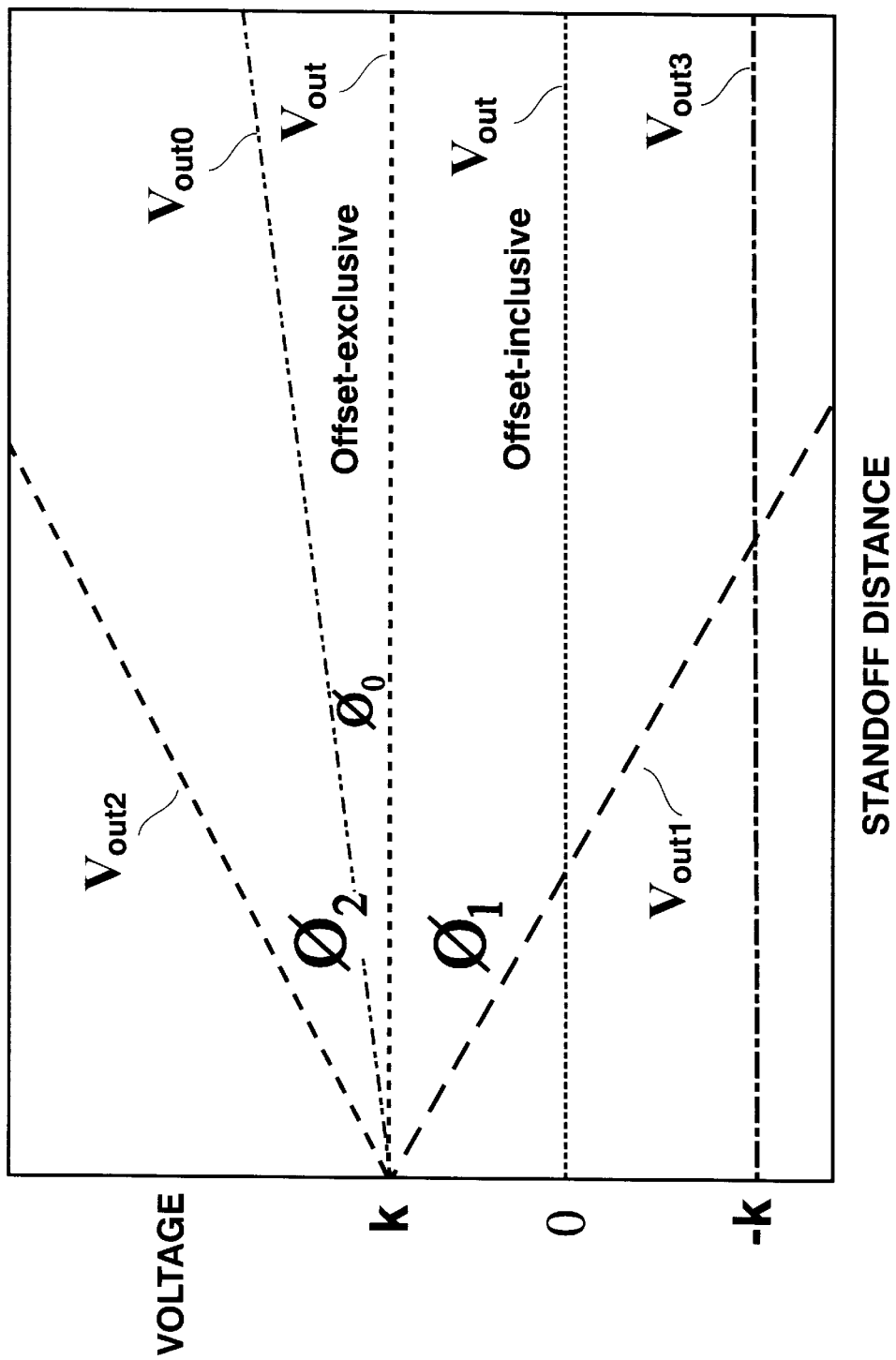
FIG. 6 is a conceptual graph of voltage (y-axis) versus standoff distance (x-axis), further illustrative of how standoff dependency may be removed in accordance with the present invention.

Reference is now made to FIG. 5 and FIG. 6, which pertain to inventive circuitry 500 having operational amplifiers characterized by polarities which are opposite those shown for operational amplifiers 10, 20, 30 and 40 in FIG. 3 and FIG. 4. With reference to. FIG. 5, the inventive removal of standoff dependency can perhaps be better understood by considering the depicted set of curves obtained in a PSPICE simulation of an embodiment of an inventive circuit 500. PSPICE is a computer program which permits performance of computer simulations of electronic circuits. The program supports schematic entry and provides graphical output, and can do several types of circuit analyses. "SPICE" stands for "Simulation Program for Integrated Circuits Emphasis." PSpice® is a commercially available PC version of Spice, made by MicroSim Corp., which in recent years merged with OrCAD, Inc.

In the plot shown in FIG. 5, changing time models changing standoff distance d; the x-axis of time directly corresponds to standoff distance d. In this plot, the signals have been shifted to show them on the same plot. The voltage $V_{out1}$, derived from the potentiometer 100 portion of inventive circuit 500, was modeled as a piecewise linear voltage source that corresponded to experimental values measured with proportionality subcircuit 1 (which includes potentiometer 100) in the lab at several points of standoff distance d. A shifted version of voltage $V_{out1}$ is shown in the linear curve indicated as curve "$V_{out1}$." The experimental values of the crystal detector 51 voltage $V_{out0}$ at each standoff distance d were also modeled Using another piecewise linear voltage, as shown in the linear curve indicated as curve "$V_{out0}$."

It is noted that, as shown in FIG. 5, these two voltages have slopes with opposite signs; that is, voltage $V_{out1}$ is negatively sloped, whereas $V_{out0}$ is positively sloped. Therefore, by multiplying the crystal detector 51 voltage $V_{out0}$ by an appropriate factor and adding it to the potentiometer-related voltage $V_{out1}$, the effect of standoff distance d can be eliminated. Appropriately changing or adjusting $R_{vary}$ in inventive circuit 500 sets this multiplication factor, which is the mathematical expression $[1+(R_{vary}+R7)/R8]$. By doing this, the output voltage $V_{out0}$ (represented by curve "$V_{out0}$") can be transformed into another output voltage (viz., output voltage $V_{out2}$) in order that the final output voltage (viz., output voltage $V_{out}$) be made independent of standoff distance d.

With reference to FIG. 6, output voltage $V_{out0}$ has become output voltage $V_{out2}$, which defines a positively sloped line having angle $θ_2$ with respect to the x-axis. In FIG. 6, which is generally conceptually illustrative of neutralization of standoff distance d in accordance with the present invention, output voltage $V_{out2}$ can be considered to be based on an original output voltage $V_{out0}$ such as output voltage $V_{out0}$ shown in FIG. 5. Output voltage $V_{out0}$ defines a positively sloped line having an angle $θ_0$ with respect to the x-axis, wherein angle $θ_0$ is smaller than angle $θ_2$. Output voltage $V_{out1}$ defines a negatively sloped line having angle $θ_1$ with respect to the x-axis. Angle $θ_1$ equals angle $θ_2$.

Therefore, when output voltage $V_{out2}$ is added to Output voltage $V_{out1}$, the net result is a zero-sloped (horizontal) line corresponding to offset-exclusive final output voltage $V_{out}$ and having an output voltage value k. The absolute value of offset-exclusive final output voltage $V_{out}$ equates as follows:

$$|V_{out}|=V_{out1}+V_{out0}[1+(R_{vary}+R7)÷R8]=V_{out1}+V_{out2}=k.$$

If an offset output voltage $V_{out3}$ is entered into the equation whereby $V_{out3}$ has an output voltage value −k and whereby output voltage $V_{out1}$ and output voltage $V_{out2}$ and output voltage $V_{out3}$ are added together, the net result is a zero-sloped (horizontal) line corresponding to offset-inclusive final output voltage $V_{out}$. The absolute value of offset-inclusive final output voltage $V_{out}$ equates as follows:

$$|V_{out}|=V_{out1}+V_{out0}[1+(R_{vary}+R7)\div R8]+V_{out3}=V_{out1}+V_{out2}+V_{out3}=k+(-k)=0$$

As shown in FIG. 6, offset output voltage $V_{out3}$, offset-inclusive final output voltage $V_{out}$ and offset-exclusive final output voltage $V_{out}$ are horizontal (parallel to each other and to the x-axis), but are characterized by different constant voltages (y-axis values). Accordingly, regardless of whether or not offset output voltage $V_{out3}$ has been introduced, the original output voltage $V_{out0}$ has been rendered independent of standoff distance d. The output voltage $V_{out}$ will be insensitive to standoff distance d, but will be sensitive to changes (e.g., defects) in material 60. However, it will generally facilitate inventive practice to calibrate inventive circuit 500 via an output voltage $V_{out3}$, so that the readings are referenced to a particular voltage (e.g., zero voltage) and thereby rendered more meaningful to the practitioner.

Offset-inclusive final output voltage $V_{out}$ is seen to lie directly and equidistantly between offset-exclusive final output voltage $V_{out}$ and offset voltage $V_{out3}$. Voltage value k represents the difference between offset-exclusive final output voltage $V_{out}$ (which equates to k voltage) and offset-inclusive final output voltage $V_{out}$ (which equates to zero voltage). Voltage value k also represents the difference between offset-inclusive final output voltage $V_{out}$ (which equates to zero voltage) and output voltage $V_{out3}$ (which equates to -k voltage). Voltage value 2k represents the difference beween offset-exclusive final output voltage $V_{out3}$ (which equates to k voltage) and output voltage $V_{out3}$ (which equates to -k voltage).

In the light of this disclosure, it is readily understood by the ordinarily skilled artisan that the present invention may be practiced in association with any and all types of near-field sensing devices. Although an inventive embodiment is described herein in relation to a near-field sensor employing microwave radiation, it is emphasized that the present invention is applicable or adaptable to near-field sensing or near-field sensors which employ practically any kind of electromagnetic radiation (waves), including but not limited to microwave radiation (waves).

Other embodiments of this invention will be apparent to those skilled in the art from a consideration of this specification or practice of the invention disclosed herein. Various omissions, modifications and changes to the principles described may be made by one skilled in the art without departing from the true scope and spirit of the invention which is indicated by the following claims.

What is claimed is:

1. For use in association with a sensing device which is capable of transmitting and receiving electromagnetic radiation for inspecting an object, said sensing device including a detector for producing a signal which is indicative of said electromagnetic radiation, apparatus comprising a distance-correction circuit which is adaptable to being in connection with said detector so that said distance-correction circuit adjusts said output voltage signal so as to account for variation in said output voltage signal due to variation in the distance of said sensing device from said object, wherein in the absence of said distance-correction circuit said detector produces a distance-dependent voltage output signal, said distance-dependent voltage output signal being variable in accordance with said distance, and wherein in combination with said distance-correction circuit said detector produces a distance-independent voltage output signal, said distance-independent voltage output signal being invariable in accordance with said distance.

2. Apparatus as recited in claim 1, wherein said distance-dependent voltage output signal varies linearly in accordance with said distance.

3. Apparatus as recited in claim 1, wherein said distance-correction circuit includes:
   a proportionality subcircuit, for producing a counteractive voltage output signal which is variable in accordance with said distance so that said distance-dependent voltage output signal and said counteractive voltage output signal vary in accordance with said distance in generally opposite manners;
   a compensation subcircuit, for modifying said distance-dependent voltage output signal so as to become a modified voltage output signal so that said modified voltage output signal and said counteractive voltage output signal vary in accordance with said distance in commensurately opposite manners; and
   a summation subcircuit, for combining said counteractive voltage output signal and said modified voltage output signal so as to result in said distance-independent voltage output signal.

4. Apparatus as recited in claim 3, wherein said distance-dependent voltage output signal, said counteractive voltage output signal, said modified voltage output signal and said distance-independent voltage output signal each vary linearly in accordance with said distance.

5. Apparatus as recited in claim 4, wherein the absolute value of the slope defined by said modified voltage output signal is equal to the absolute value of the slope defined by said counteractive voltage output signal.

6. Apparatus as recited in claim 3, wherein said proportionality subcircuit includes potentiometer means for being indicative of variation in said distance.

7. Apparatus as recited in claim 3, wherein said proportionality subcircuit includes a spring-loaded piston potentiometer which physically contacts said object so as to be indicative of variation in said distance.

8. Apparatus as recited in claim 3, wherein:
   said compensation subcircuit includes a variable resistor having a resistance $R_{vary}$;
   said distance-dependent voltage output signal has a voltage $V_{orig}$;
   said modified voltage output signal has a voltage $V_{mod}$; and
   said voltage $V_{mod}$ is a function of the product of said voltage $V_{orig}$ and an expression which includes said resistance $R_{vary}$.

9. Apparatus as recited in claim 8, wherein:
   said counteractive voltage output signal has a voltage $V_{counter}$; and
   the absolute value of the slope described by voltage $V_{counter}$ equals the absolute value of the slope described by $V_{mod}$.

10. Apparatus as recited in claim 3, wherein:
    said compensation subcircuit includes an operational amplifier, said operational amplifier including a first resistor having a nonvariable resistance $R_{nonvary1}$, a second resistor having a nonvariable resistance $R_{nonvary2}$ and a third resistor having a variable resistance $R_{vary}$;
    said distance-dependent voltage output signal has a voltage $V_{orig}$;
    said modified voltage output signal has a voltage $V_{mod}$; and $$V_{mod}=V_{orig}[1+(R_{vary}+R_{nonvary1})/R_{nonvary2}].$$

11. Apparatus as recited in claim 10, wherein:

said counteractive voltage output signal has a voltage $V_{counter}$; and the absolute value of the slope defined by voltage $V_{counter}$ equals the absolute value of the slope defined by $V_{mod}$.

12. Apparatus as recited in claim 3, wherein said distance-correction circuit includes:

a proportionality subcircuit, for producing a counteractive voltage output signal which is variable in accordance with said distance so that said distance-dependent voltage output signal and said counteractive voltage output signal vary in accordance with said distance in generally opposite manners;

a compensation subcircuit, for modifying said distance-dependent voltage output signal so as to become a modified voltage output signal so that said modified voltage output signal and said counteractive voltage output signal vary in accordance with said distance in commensurately opposite manners;

an offset subcircuit for producing an offset voltage output signal which is invariable in accordance with said distance; and a summation subcircuit for combining said counteractive voltage output signal, said modified voltage output signal and said offset voltage output signal so as to result in said distance-independent voltage output signal.

13. Apparatus as recited in claim 12, wherein said distance-dependent voltage output signal, said counteractive voltage output signal, said modified voltage output signal, said offset voltage output signal and said distance-independent voltage output signal each vary linearly in accordance with said distance.

14. Apparatus as recited in claim 12, wherein said offset subcircuit is for producing a said offset voltage output signal having a selected voltage, thereby resulting in a said distance-independent voltage output signal having a selected voltage.

15. Apparatus as recited in claim 12, wherein:

said counteractive voltage output signal has a voltage $V_{counter}$;

said modified voltage output signal has a voltage $V_{mod}$;

said offset voltage output signal has a voltage $V_{offset}$;

said distance-independent voltage output signal has a voltage V; and

V=one of $$(V_{counter}+V_{mod}+V_{offset})$$

and $$-(V_{counter}+V_{mod}+V_{offset}).$$

16. Apparatus as recited in claim 15, wherein said offset subcircuit is for producing a said offset voltage output signal having a selected voltage $V_{offset}$, thereby resulting in a said distance-independent voltage output signal having a selected voltage V.

17. Apparatus as recited in claim 16, wherein said offset subcircuit includes a resistor having a variable resistance $R_{offset}$, and wherein voltage $V_{offset}$ is a function of resistance $R_{offset}$.

18. Apparatus as recited in claim 15, wherein:

said distance-dependent voltage output signal has a voltage $V_{orig}$;

said compensation subcircuit includes a resistor having a resistance $R_{vary}$; and said voltage $V_{mod}$ is a function of the product of said voltage $V_{orig}$ and an expression which includes said resistance $R_{vary}$.

19. Apparatus as recited in claim 15, wherein:

said distance-dependent voltage output signal has a voltage $V_{orig}$;

said compensation subcircuit includes an operational amplifier, said operational amplifier including a first resistor having a nonvariable resistance $R_{nonvary1}$, a second resistor having a nonvariable resistance $R_{nonvary2}$ and a third resistor having a variable resistance $R_{vary}$; and $$V_{mod}=V_{orig}[1+(R_{vary}+R_{nonvary1})/R_{nonvary2}].$$

20. Apparatus as recited in claim 19, wherein:

said offset subcircuit is for producing a said offset voltage output signal having a selected voltage $V_{offset}$, thereby resulting in a said distance-independent voltage output signal having a selected voltage V;

said offset subcircuit includes a resistor having a variable resistance $R_{offset}$; and said voltage $V_{offset}$ is a function of said resistance $R_{offset}$.

21. Apparatus as recited in claim 1, wherein:

said object has an object surface area which faces said sensing device;

said sensing device has a device opening for permitting said transmitting and said receiving of said electromagnetic radiation; and said distance is the distance from said device opening to said object surface area.

22. Apparatus as recited in claim 21, wherein:

said surface area is characterized by a degree of surface roughness;

said distance varies in accordance with said surface roughness; and said distance-independent voltage output signal is invariable in accordance with said surface roughness.

23. Apparatus as recited in claim 1, wherein:

said object has an object surface characterized by a degree of surface roughness;

said sensing device is movable in a direction parallel to said object surface;

said distance-correction circuit includes a piston potentiometer which is coupled with said sensing device and which contactingly traverses said object surface while said sensing device is moving in said direction parallel to said object surface, said piston potentiometer thereby being indicative of variation in said distance which is attributable to said surface roughness; and said distance-independent voltage output signal is the aggregation of plural component voltage signals, said component voltage signals including a first component voltage signal and a second component voltage signal, said first component voltage signal relating to said piston potentiometer and being variable in accordance with said distance, said second component voltage signal relating to said distance-dependent voltage output signal and being variable in accordance with said distance, wherein said first component voltage signal and said second component voltage signal neutralize each other while said sensing device is moving in said direction parallel to said object surface.

24. Apparatus as recited in claim 23, wherein said component voltage signals include a third component voltage signal which is constant, said third component voltage signal being aggregated along with said first component voltage signal and said second component voltage signal so as to set said distance-independent output signal at a selected value.

25. For effectuation in association with a sensing device which is capable of transmitting and receiving electromagnetic radiation for inspecting an object, said sensing device including a detector for producing an output voltage signal which is indicative of said electromagnetic radiation, a method comprising adjusting said output voltage signal so as to account for variation in said output voltage signal due to variation in the distance of said sensing device from said object, said adjusting including connecting a distance-correction circuit with said detector, wherein:

in the absence of said distance-correction circuit said detector produces a distance-dependent voltage output signal, said distance-dependent voltage output signal being variable in accordance with said distance; and in combination with said distance-correction circuit said detector produces a distance-independent voltage output signal, said distance-independent voltage output signal being invariable in accordance with said distance.

26. A method as recited in claim 25, wherein said adjusting includes:

producing a counteractive voltage output signal, said counteractive voltage output signal varying in accordance with said distance so that said distance-dependent voltage output signal and said counteractive voltage output signal vary in accordance with said distance in generally opposite manners;

modifying said distance-dependent voltage output signal signal so as to become a modified voltage output signal so that said modified voltage output signal and said counteractive voltage output signal vary in accordance with said distance in commensurately opposite manners; and combining said counteractive voltage output signal and said modified voltage output signal;

wherein said distance-independent voltage output signal is based on said combining of said counteractive voltage output signal and said modified voltage output signal.

27. A method as recited in claim 26, wherein said distance-dependent voltage output signal, said counteractive voltage output signal, said modified voltage output signal and said distance-independent voltage output signal each vary linearly in accordance with said distance.

28. A method as recited in claim 26, wherein:

said adjusting includes producing an offset voltage output signal;

said combining signals includes combining said counteractive voltage output signal, said modified voltage output signal and said offset voltage output signal; and said distance-independent voltage output signal is based on said combining of said modified voltage output signal, said counteractive voltage output signal and said offset voltage output signal.

29. A method as recited in claim 28, wherein said distance-dependent voltage output signal, said counteractive voltage output signal, said modified voltage output signal, said offset voltage output signal and said distance-independent voltage output signal each vary linearly in accordance with said distance.

30. A method as recited in claim 29, wherein said producing an offset voltage output signal includes producing a said offset voltage output signal having a selected voltage, thereby resulting in a said distance-independent voltage output signal having a selected voltage.

31. A method as recited in claim 29, wherein:

said producing a counteractive voltage output signal includes using a potentiometer to produce a potentiometer voltage, and includes using a first operational amplifier with respect to said potentiometer voltage, said counteractive voltage output signal being related to said potentiometer voltage;

said modifying said distance-dependent voltage output signal includes using a second operational amplifier with respect to said nonconstant detector signal, said using a second operational amplifier including using a first variable resistor to establish a first resistance, said modified voltage output signal being related to said said first resistance;

said producing an offset voltage output signal includes using a third operational amplifier, said using a third operational amplifier including using a second variable resistor to establish a second resistance, said offset voltage output signal being related to said second resistance; and said combining said counteractive voltage output signal, said modified voltage output signal and said offset voltage output signal includes performing an additive operation with respect to the voltages corresponding to said counteractive voltage output signal, said modified voltage output aid offset voltage output signal.

32. Apparatus as recited in claim 25, wherein:

said object has an object surface characterized by a degree of surface roughness;

said sensing device is movable in a direction parallel to said object surface;

said adjusting includes coupling a piston potentiometer with said sensing device so as to contactingly traverse said object surface while said sensing device is moving in said direction parallel to said object surface, said piston potentiometer thereby being indicative of variation in said distance which is attributable to said surface roughness; and said adjusting includes aggregating plural component voltage signals, said component voltage signals including a first component voltage signal and a second component voltage signal, said first component voltage signal relating to said piston potentiometer and being variable in accordance with said distance, said second component voltage signal relating to said distance-dependent voltage output signal and being variable in accordance with said distance, wherein said first component voltage signal and said second component voltage signal neutralize each other while said sensing device is moving in said direction parallel to said object surface.

33. A near-field sensing device of the kind which transmits electromagnetic energy to and receives electromagnetic energy from an entity of interest during nondestructive scanning of an entity, said near-field sensing device being situated at a standoff distance from a surface of said entity and being caused to move parallel to said surface during said scanning, said surface being characterized by surface roughness which affects said standoff distance during said scanning, said near-field sensing device comprising:

a detector which outputs an initial voltage which indicates a condition of said electromagnetic radiation during said scanning, wherein during said scanning said initial voltage is dependent on said standoff distance and hence is dependent on said surface irregularity; and electronic apparatus which inputs said initial voltage and outputs a final voltage during said scanning, said electronic apparatus including a piston potentiometer which is attached to said near-field sensing device and which contacts said surface during said scanning, wherein during said scanning said piston potentiometer continually measures said standoff distance so as to result in a proportionality voltage which generally represents an additive inverse of said initial voltage, said final voltage being based on the addition of said proportionality voltage and said initial voltage whereby said final voltage is independent of said standoff distance and hence is independent of said surface irregularity.

34. The near-field sensing device according to claim 33, said electronic apparatus comprising:

a first operational amplifier which generates said proportionality voltage, said potentiometer generating a potentiometer voltage, said first operational amplifier adjusting the value of said potentiometer voltage so as to become said proportionality voltage;

a second operational amplifier which generates a compensation voltage, said second operational amplifier adjusting the value of said initial voltage so as to become said compensation voltage, whereby the respective values of said proportionality voltage and said compensation voltage additively counterbalance each other;

a third operational amplifier which generates a constant offset voltage; and a fourth operational amplifier which generates said final voltage, said fourth operation amplifier being connected to said first operational amplifier, said second operational amplifier and said third operational amplifier, said final voltage being based on the sum of the respective values of said proportionality voltage, said compensation voltage and said offset voltage.

35. The near-field sensing device according to claim 34, wherein said detector includes a crystal diode detector.

36. The near-field sensing device according to claim 34, wherein said second operational amplifier includes a first-variable resistor for performing said adjusting of the value of said initial voltage, and wherein said third operational amplifier includes a second variable resistor for selecting the value of said offset voltage.

37. The near-field device according to claim 34, wherein the value of said offset voltage selectively determines the value of said final voltage.

* * * * *